(12) United States Patent
Kido

(10) Patent No.: US 10,502,667 B2
(45) Date of Patent: *Dec. 10, 2019

(54) APPARATUSES FOR GENERATING A RECIPROCATING MOTION FOR THE PURPOSE OF GRINDING OF SAMPLES

(71) Applicant: Rotaprep, Inc., Tustin, CA (US)

(72) Inventor: Horacio Kido, Lake Forest, CA (US)

(73) Assignee: ROTAPREP, INC., Tustin, CA (US)

( * ) Notice: Subject to any disclaimer, the term of this patent is extended or adjusted under 35 U.S.C. 154(b) by 116 days.

This patent is subject to a terminal disclaimer.

(21) Appl. No.: 15/702,612

(22) Filed: Sep. 12, 2017

(65) Prior Publication Data

US 2018/0095017 A1 Apr. 5, 2018

Related U.S. Application Data

(63) Continuation of application No. 14/257,632, filed on Apr. 21, 2014, now Pat. No. 9,759,638.

(60) Provisional application No. 61/816,094, filed on Apr. 25, 2013.

(51) Int. Cl.
*B02C 17/00* (2006.01)
*G01N 1/28* (2006.01)
*B02C 17/14* (2006.01)
*B01F 11/00* (2006.01)
*B01F 13/00* (2006.01)
*B02C 17/24* (2006.01)

(52) U.S. Cl.
CPC .......... *G01N 1/286* (2013.01); *B01F 11/0008* (2013.01); *B01F 11/0014* (2013.01); *B01F 13/0028* (2013.01); *B01F 13/0052* (2013.01); *B02C 17/00* (2013.01); *B02C 17/14* (2013.01); *B02C 17/24* (2013.01); *G01N 2001/2866* (2013.01)

(58) Field of Classification Search
CPC .. B02C 17/00; B02C 17/14; G01N 2001/2866
USPC .................................................. 241/170–181
See application file for complete search history.

(56) References Cited

U.S. PATENT DOCUMENTS 2,247,978 A * 7/1941 Van Arkel ........... B01F 11/0031
241/175
4,305,668 A * 12/1981 Bilbrey ................... B01F 11/00
366/111
5,567,050 A * 10/1996 Zlobinsky ........... B01F 11/0008
366/110

(Continued)

*Primary Examiner* — Faye Francis
(74) *Attorney, Agent, or Firm* — Chang & Hale LLP

(57) ABSTRACT

Disclosed herein are devices, apparatuses, and methods for generating a reciprocating motion for the purpose of grinding or homogenizing samples. An apparatus includes a connecting linkage that extends along a longitudinal axis. The apparatus includes a sample vial holder attached to the connecting linkage. The apparatus includes a crank operatively connected to the proximal end of the connecting linkage, the crank configured to impart rotational motion to the proximal end of the connecting linkage. The apparatus includes a sliding carriage operatively connected to the distal end of the connecting linkage, the sliding carriage configured to restrict the distal end of the connecting linkage to a linear path. The apparatus includes a motor operatively connected to the crank to rotate the crank such that the sample vial holder, in use, moves with a combination of rotational and linear motion.

20 Claims, 3 Drawing Sheets

(56) References Cited

U.S. PATENT DOCUMENTS

| | | | | |
|---|---|---|---|---|
| 6,880,771 B2* | 4/2005 | Deppermann | .......... | B02C 17/10 |
| | | | | 241/175 |
| 7,448,566 B2* | 11/2008 | Bysouth | ................ | B01F 9/0001 |
| | | | | 241/175 |
| 7,823,818 B2* | 11/2010 | Stitt | ........................ | B02C 17/10 |
| | | | | 241/171 |
| 8,016,218 B1* | 9/2011 | Friedman | ............ | B01F 11/0017 |
| | | | | 241/175 |
| 8,201,765 B2* | 6/2012 | Rajagopal | .............. | C12M 47/06 |
| | | | | 241/172 |
| 9,962,717 B1* | 5/2018 | Micic | .................... | B04B 5/0421 |
| 2003/0146313 A1* | 8/2003 | Deppermann | .......... | B02C 17/10 |
| | | | | 241/30 |
| 2007/0036025 A1* | 2/2007 | Friedman | ............ | B01F 11/0034 |
| | | | | 366/208 |
| 2009/0101738 A1* | 4/2009 | Stitt | ........................ | B02C 17/10 |
| | | | | 241/23 |
| 2010/0181402 A1* | 7/2010 | Mahler | ................... | B02C 17/14 |
| | | | | 241/179 |
| 2012/0263010 A1* | 10/2012 | Boquet | ............... | B01F 11/0008 |
| | | | | 366/110 |

* cited by examiner ns for Analysis," which claims the benefit of priority
APPARATUSES FOR GENERATING A RECIPROCATING MOTION FOR THE PURPOSE OF GRINDING OF SAMPLES

CROSS-REFERENCE TO RELATED APPLICATIONS

This is a continuation of U.S. application Ser. No. 14/257,632 (issued as U.S. Pat. No. 9,759,638) filed Apr. 21, 2014 and entitled "Apparatus and Method for Grinding of Samples for Analysis," which claims the benefit of priority to U.S. Provisional Application No. 61/816,094 filed Apr. 25, 2013 and entitled "Mechanism for Grinding of Biological Samples," each of which is expressly incorporated by reference herein in its entirety for all purposes.

BACKGROUND

Field

The present invention is directed to hand held and table top grinders and homogenizers such as those used to release proteins and nucleic acids from biological samples and those that grind geological samples for composition analysis. Samples may include, for example, seeds, soil, bones, teeth, tissues, spores, yeasts, and gram positive microbes. Certain embodiments, described below, result in more efficient and faster processing of said samples.

The most commonly used homogenizers are of the bead mill type (bead-beater), in which a biological or geological sample is added to a container such as a sample vial or tube that is preloaded with grinding media such as, but not limited to, for example, ceramic, glass or metal beads. A special buffer designed to dissolve proteins, nucleic acids, minerals and/or metals may also be added, followed by sealing of the tube typically with a screw cap. The sealed tube is then placed into the homogenizer, which mechanically agitates it in an oscillatory manner, causing the media (hard beads) within the tube to impact and break the sample. Typical rates of oscillation are in the range of 4,000 to 5,000 cycles per minute. This grinding or homogenization of the sample facilitates the extraction of proteins, nucleic acids, metals and/or minerals for use in downstream processes such as amplification, analysis of DNA and/or analysis of metal/mineral composition.

The biggest drawback with most bead mill homogenizers is that their range of oscillatory motion is not high enough to cause the beads to traverse the whole length of the sample processing chamber such as a sample vial or tube. Furthermore, if the sample tube is oriented vertically in the homogenizer, gravity tends to cause the beads to localize at the bottom of the tube during homogenization. At the same time, the biological sample, which is less dense than the beads will tend to stay closer to the top of the tube. As a result, the time to achieve complete homogenization is long, usually in the range from 5 to 60 seconds; perhaps longer if the sample is also hard (e.g. dry corn kernel, bone, etc.). Another undesired effect from this inefficient homogenization scheme is the generation of heat proportional to the length of time of homogenization due to internal friction within the tube. This heat is problematic if the desired nucleic acids are RNAs, which quickly degrade at elevated temperatures.

The previously mentioned drawbacks could be mitigated if the amplitude of oscillatory motion were to be extended to be at least equal to the length of the tube being used to process a biological sample such as that in the apparatus of the present invention. Doing so would cause the milling beads within the tube to traverse the whole length of the tube, enhancing the incidence of encounters between the beads and the sample. This more efficient design of the apparatus of the present invention in turn results in shorter homogenization times and thus, less heat generation. The preferred embodiment of the present invention has substantially improved grinding/homogenization efficiency, leading to shorter homogenization times, and less heat generation compared to those in the prior art.

Description of Related Art

There are a number of bead mill homogenizers (bead-beaters) on the market including that disclosed in U.S. Pat. No. 5,567,050, entitled "Apparatus and method for rapidly oscillating specimen vessels", which describes an apparatus and method for rapidly oscillating specimen containing vessels such as those used in an RNA recovery operation wherein small sized glass sized beads in the vessel are employed to disrupt the cell walls of an RNA component to release the RNA, includes a specimen vessel holder provided as a disc in which the containers are received. The disc is operably connected with oscillatory motion producing means that in operation oscillates the disc rapidly in an oscillatory movement up and down symmetrically of a fixed vertical axis. The disc is haltered so it cannot rotate about the fixed axis. Locking means in the form of a locking plate locks the vessels on the vessel holder and applies a clamping force thereto to prevent relative movement between the vessels and the holder to prevent generation of heat that could be of deleterious effect to the specimen material or the vessels holding same.

Another example of a bead beater is described in U.S. Patent Application Publication No. 2012/0263010, entitled "Device for the Quick Vibration of Tubes Containing, In Particular, Biological Samples" which discloses an appliance for rapidly vibrating test tubes containing samples to be ground up, the appliance comprising an electric motor for driving rotation of a disk that is provided with an eccentric pin, the appliance being characterized in that the test tubes are perpendicular to the eccentric pin and are held by a clamp mounted on a support that is substantially parallel to the eccentric pin, being connected to a fixed baseplate via a Cardan type hinge having two mutually perpendicular axes of rotation (X and Y), one of which axes (Y) is substantially parallel to the eccentric pin and connects the support to the other axis (X) of the hinge that prevents the support from moving in rotation about a perpendicular axis (Z). The support is connected to the eccentric pin by a link.

Both of the above devices produce a FIG. 8 motion, with respective capacities of 12×2 mL and 3×2 mL sample tubes/vials, and peak to peak amplitudes of ⅝ and ¾ inch. Since the sample tubes/vials in both examples are 1.5 inches tall, this means that the sample and hard matrices do not have the opportunity to travel throughout the whole length of the sample vial and they stay mostly at the bottom of the sample vial. In contrast, the apparatus of the present invention produces an elliptical motion/path and has a peak to peak amplitude equal to the length of the sample vial (1.5 inches, for example) allowing the matrices to fully interact with the sample throughout the sample tube/vial (sample processing chamber), making it much more efficient, achieving the same results, as the devices above, in about 1/10th the time of the other bead mill/bead-beater homogenizers.

Table 1 below outlines characteristics of commonly used sample grinders and homogenizers, for example, including a preferred embodiment of the apparatus of the present invention showing the peak to peak amplitude advantage of the present invention. The peak to peak amplitude of the present invention is not limited to 1.5 inches but is shown only as an example. Peak to peak amplitude can be adjusted in the apparatus of the present invention to match the sample processing chamber (sample vial) length by varying the diameter of its crank to match the length of the sample processing chamber.

TABLE 1

| Product | Type | Action | Sample throughput | Frequency Range (cpm) | Amplitude (inches) |
|---|---|---|---|---|---|
| Present Invention | Bead-Beater | crank-slider (combination of circular and linear motion) | 1 | 750-4,400 | 1.5 |
| Xpedition | Bead-Beater | vertical linear impaction | 1 | 3,600 | 0.25 |
| Tissue-Tearor | Rotor-stator | probe rotor-stator | 1 | 5,000-35,000 | n/a |
| Shredder SG3 | Pressure | hydraulic forcing of sample through a sieve with simultaneous rotational mechanical grinding | 1 | 200 | n/a |
| Disruptor Genie | Bead-Beater | horizontal orbital motion | 12 | 1,000-3,000 | 0.5 |
| Bead-Bug | Bead-Beater | Arc-shaped trajectory (~2 inch radius) | 3 | 2,700-4,000 | 0.75 |
| Mini-Bead beater-1 | Bead-Beater | Arc-shaped trajectory (~2 inch radius) | 1 | 2,500-4,800 | 0.75 |
| Bullet Blender (BBX6F) | Bead-Beater | Horizontal linear impaction | 24 | 100-1,200 | 0.125 |
| TissueLyserLT | Bead-Beater | Vertical linear motion | 12 | 900-3,000 | 0.75 |
| PRECELLYS*24 | Bead-Beater | Arc-shaped trajectory (~3 inch radius) | 24 | 6,500 | 0.315 |
| MINILYS | Bead-Beater | Arc-shaped trajectory (~3 inch radius) | 3 | 3,000, 4,000, 5,000 | 0.63 | may include multiple holders. The diameter of the crank is equal to or greater than the axial length of the sample vial (if the sample vial is 1.5 inches then the crank diameter will be 1.5 inches or greater), so the crank diameter preferably corresponds to the axial length of the sample vial or tube. For example, when a 1.5 inch sample vial is inserted into the holder, it will undergo an elliptical oscillatory motion (elliptical path) with peak to peak amplitude of 1.5 inches, causing the grinding matrices and sample within the sample vial or tube to traverse the whole length of the sample vial or tube thereby maximizing cascade impaction and shearing forces. With the other previously described bead-beaters, the matrices (beads) and samples tend to stay localized at the bottoms of the sample vial or tube, strongly influenced by gravity, which tends to separate the heavy matrices from the lighter matrices into a density gradient.

Another important characteristic that gives the apparatus of the present invention an advantage over the other bead-beaters is that the sample vial or tube in the apparatus of the present invention is rigidly held at the top and bottom, making the collisions (during change of axial direction) at those extremities mostly inelastic. This means that most energy will go into cascade collisions instead of moving the tube or the tube holder. The impaction-based bead-beaters experience inelastic collisions mostly at the time of impaction. The rest of the time, the matrices and samples are colliding elastically within the tube. This makes processing with those bead-beaters much more inefficient and time-consuming.

The present invention is specifically directed to a mechanical reciprocating apparatus for grinding of samples comprising one or more sample vials or tubes of predetermined length, a grinding media in the sample vial, a holder to hold the sample vial, a connecting linkage where said holder is attached to, said connecting linkage having a distal and proximal end with pivot points at each end, a crank pivot connected to the proximal end of said connecting linkage, a slide pivot connected to the distal end of said connecting

SUMMARY

The present invention is an apparatus that generates a reciprocating motion for the purpose of grinding, or homogenizing (if liquid is present), biological or geological samples. A motor-driven crank is linked to a linearly-confined carriage via a connecting linkage. The linkage contains a holder for a sample tube or vial. The sample vial is preferably cylindrical or rectangular in shape. As the crank rotates, the sample vial in the holder experiences an elliptical oscillatory reciprocating motion that causes the sample and grinding media, such as, for example ceramic beads, within the sample vial to collide with each other as they traverse the length of the sample vial. The sample breaks apart as a result of the collisions with the beads. The invention allows for substantial reduction of process time down to the range of 1 to 5 seconds versus 5 to 60 seconds for bead-beaters commonly used by laboratories, using the same reciprocation rates of about 4,000 to 5,000 cycles per minute.

Compared to the above-mentioned bead-beaters, the apparatus of the present invention stands apart because it is more efficient and therefore about 1 order of magnitude shorter processing times than other bead-beaters. Its mechanism consists of a rotating crank connected to a slider via a connecting linkage (linkage). A holder for a sample vial or tube is attached to middle of the connecting linkage, which is approximately 7.3 inches long in a preferred embodiment of the present invention but can be longer or shorter depending on the desired elliptical path and the number of holders attached thereto, i.e., the apparatus of the present invention linkage, a frame top and a bottom frame wherein the various components of the apparatus are attached, a sliding carriage on a rail that is affixed to the frame top, said sliding carriage is connected to the slide pivot, a crank having a diameter equal to or greater than the length of the sample vial, said crank attached to the crank pivot; and a motor operatively connected to the crank. The connecting linkage may also accommodate multiple holders and the holders may be placed at various distances (adjustable) from the ends of the connecting linkage to optimize its elliptical path of samples in the sample vial. In addition to varying the location of the holder/tube on the connecting linkage, the length of the connecting linkage and the diameter of the crank may also be varied and optimized to achieve an optimal sample/sample vial and/or media path to allow efficient grinding of the samples. The rail of the apparatus of the present invention may alternatively be attached to the connecting linkage and the sliding carriage may be fixed to a pivot point on the frame top of the apparatus instead of the sliding carriage. Many types of commercially available sample vials may be used in the present invention including, for example, but not limited to, cryogenic tubes, multi-well plates, plastic, metal or glass vials, and other sample processing tubes/vials such as those listed in Table 2, below. Different types of motors may also be used for the present invention including, for example; electrically, pneumatically, or hydraulically driven motors. The apparatus of the present invention may be configured as a hand held device or a table top device depending on its capacity for holding multiple sample vials or tubes.

TABLE 2

| Model # | Description | Capacity (mL) | Skirt | Vendor |
|---|---|---|---|---|
| 72.693 | Screw cap tube | 2 | no | Sarstedt |
| 72.694 | Screw cap tube | 2 | yes | Sarstedt |
| 72.730.406 | Screw cap tube | 0.5 | yes | Sarstedt |
| 72.730.406 | Screw cap tube | 1.5 | yes | Sarstedt |
| 330TX | Screw cap tube with extra thick walls | 2 | no | Biospec |
| 2007 | Stainless steel tubes | 2 | no | Biospec |
| S6003-50 | Lysis tubes prefilled with 2.0 mm diameter ceramic balls | 2 | yes | Zymo Research |
| S6002-50 | Lysis tubes prefilled with 0.5 mm diameter ceramic balls | 2 | yes | Zymo Research |

BRIEF DESCRIPTION OF THE DRAWINGS

Further objects of the present invention together with additional features contributing thereto and advantages accruing therefrom will be apparent from the following description of the preferred embodiments of the invention which are shown in the accompanying drawing figures with like reference numerals indicating like components throughout wherein.

DETAILED DESCRIPTION OF SOME EMBODIMENTS

Figure 1:
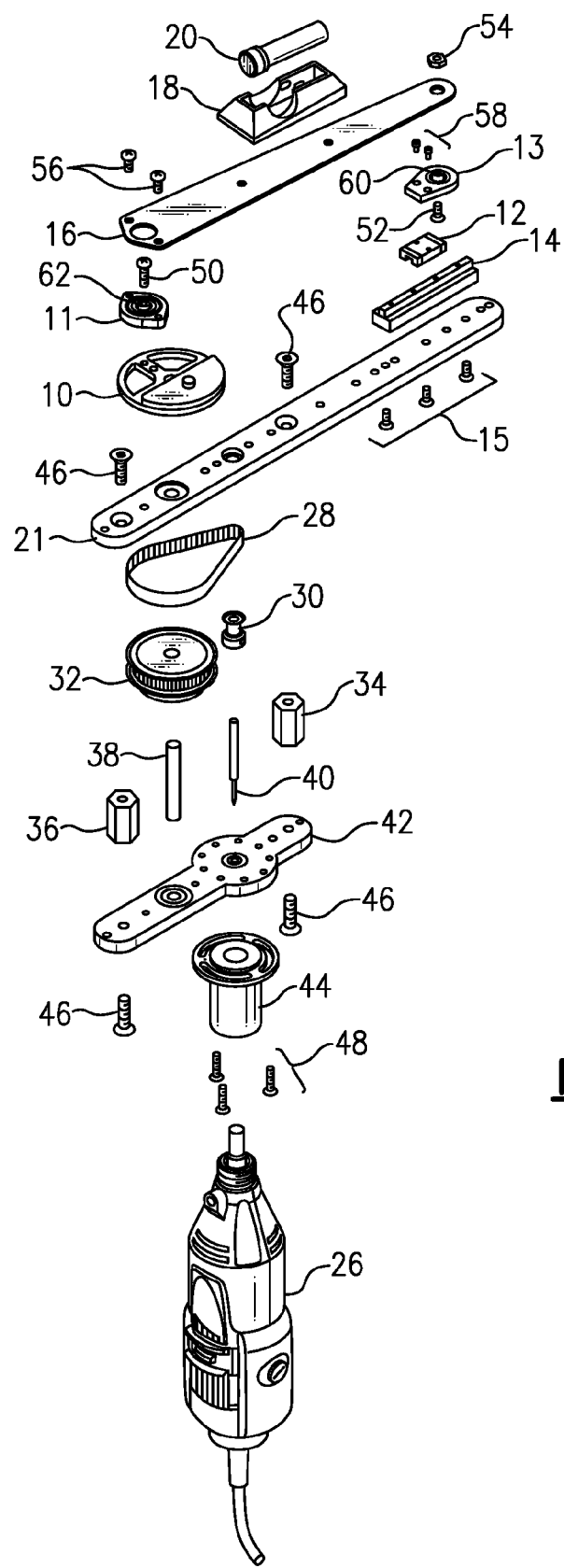
FIG. 1 is blow-up illustration of the apparatus of the present invention showing the individual components thereof.

The components of the preferred embodiment of the apparatus of the present invention are shown in the blown-up illustration of FIG. 1. The individual components of the apparatus, with like reference numbers corresponding to the drawing of FIG. 1, are listed below in Table 3:

TABLE 3

| Ref No. | Description |
|---|---|
| 10 | crank |
| 11 | crank pivot |
| 12 | sliding carriage/carriage/slide |
| 13 | slide pivot |
| 14 | rail |
| 15 | rail screws |
| 16 | linkage or connecting linkage |
| 18 | holder |
| 20 | sample vial or tube |
| 21 | frame top |
| 22 | ceramic bead |
| 26 | motor |
| 28 | drive belt |
| 30 | small pulley |
| 32 | big pulley |
| 34 | spacer |
| 36 | spacer |
| 38 | big pulley shaft |
| 40 | small pulley shaft |
| 42 | frame bottom |
| 44 | threaded adapter |
| 46 | frame screws |
| 48 | adapter screws |
| 50 | crank pivot bolt |
| 52 | slide pivot bolt |
| 54 | slide pivot nut |
| 56 | top frame screw |
| 58 | slide pivot carriage screw |
| 60 | slide pivot bearing |
| 62 | crank pivot bearing |
| 100 | reference line |

As illustrated in FIG. 1, a sample tube or vial (20) fits inside a holder (18). The holder (18) is attached to a connecting linkage or linkage (16). The linkage (16) sits on top of bearing pivots; the crank pivot (11) and slide pivot (13). The proximal end of the linkage (16) is attached to the crank pivot (11) via the top frame screws (56) while its distal end is attached to the slider pivot bearing (60) in the slider pivot (13) and is held in place via the slide pivot bolt (52) and slide pivot nut (54). The slide pivot (13) is connected to the sliding carriage or slide (12) via slide pivot carriage screws (58). The slide (12) sits on top of the rail (14) which is attached to the frame top (21) via slide screws (15). The crank pivot (11) is attached to the crank (10) via a crank pivot bearing (62). The crank (10) is connected to the big pulley (32) via the big pulley shaft (38). The big pulley (32) is driven or turned via a small pulley (30) through a drive belt (28). The small pulley (30) is connected to a small pulley shaft (40) which connects directly to the motor (26). The big pulley (32), big pulley shaft (38), drive belt (28) and the small pulley (30) are held in place between the frame top (21) and frame bottom (42) via frame screws (46) and spacers (34 and 36). The frame bottom (42) is attached to a threaded motor adapter (44) via adapter screws (48). The threaded motor adapter (44) allows for the attachment of the device of the present invention to the motor (26) which drives the small pulley (30) thereby moving the sample vial (20) in an elliptical path at a predetermined rate. In an alternate embodiment of the present invention, the sliding carriage (12) and rail (14) is made longer so that the holder (18) could be placed directly on the sliding carriage (12). The motion of the sample vial (20) is linear in this alternative embodiment.

Figure 2:
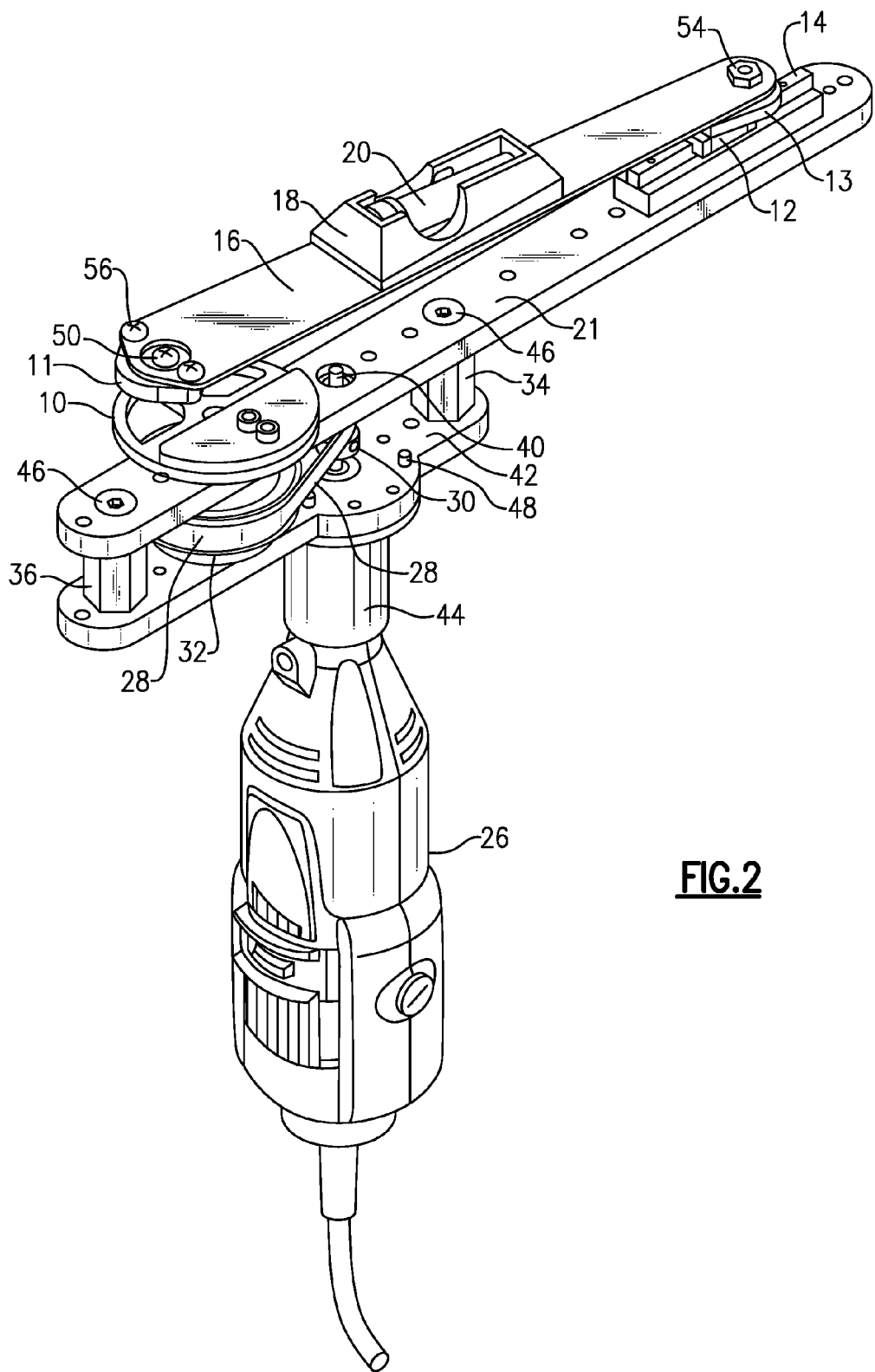
FIG. 2 is an isometric view of the apparatus of the present invention.

With reference now to FIG. 2, there is depicted an isometric view of a fully assembled apparatus of the present invention with the sample vial (20) in vial holder (18) which is in turn mounted on the connecting linkage (16), which has a pivot point at each end for connecting it to sliding carriage (12) at the distal end and crank 10 at the proximal end as shown in FIG. 2. Slide/carriage (12) slides on rail (14), which is fixed to the frame top (21) of the apparatus as discussed above. Motor (26) is linked to crank (10) via small pulley (30), drive belt (28), and big pulley (32). As crank (10) is driven to rotate by motor (26), its rotational motion is converted to linear motion as carriage (12) slides on rail (14). Since holder (18) is placed approximately halfway between the crank (10) and carriage (12), it experiences a combination of linear and rotational motion, resulting in an elliptical trajectory of sample vial/tube (20).

The next figures, FIGS. 3A-3D, shows a top view of the apparatus at four angular positions of the cycle of crank (10), as it rotates in a counterclockwise direction, is presented in FIGS. 3A-3D. Also illustrated is a ceramic bead (22) that acts as pestle in grinding samples placed in the sample vial (20). Since the ceramic bead (22) has a high finite inertia, it will tend to stay in place at the level of reference line (100) while vial (20) surrounding it reciprocates in an elliptical path.

Figures 3A, 3B, 3C, 3D:
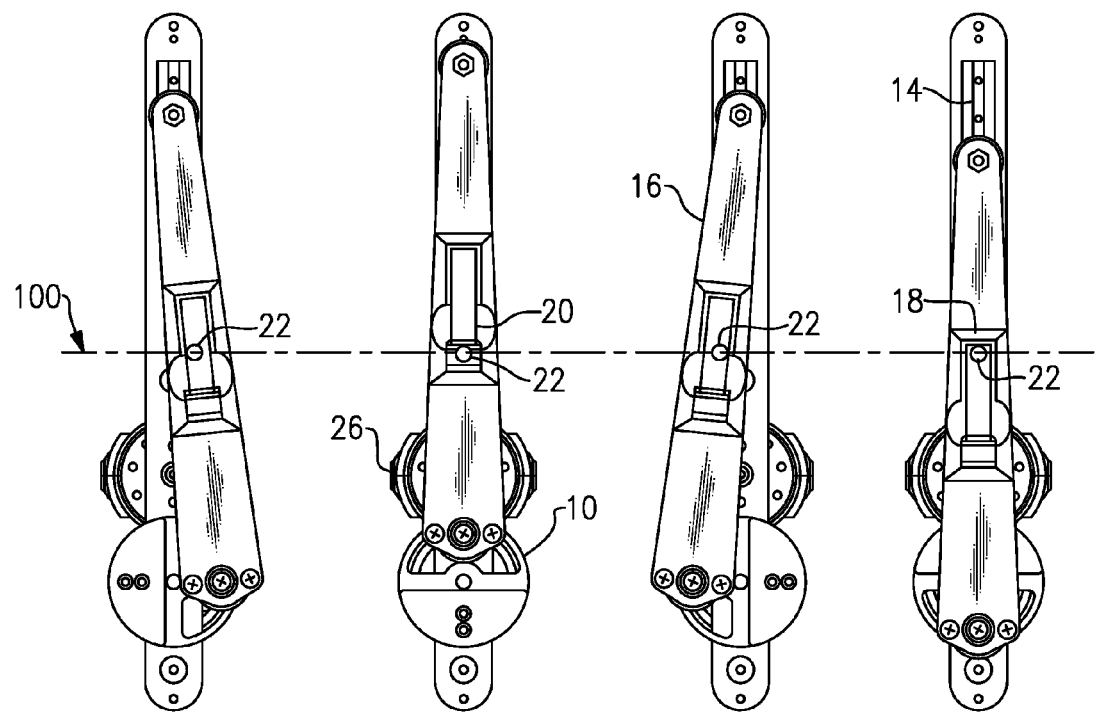
FIGS. 3A, 3B, 3C, and 3D are a top view of the apparatus of the present invention at four different angular positions of the crank.

Specifically, FIG. 3A depicts the ceramic bead (22) at midway the length of the vial (20), pressed against its left wall as it travels towards the top. FIG. 3B depicts the bead (22) impacting the top end of the tube. FIG. 3C depicts the ceramic bead (22) again midway the length of the tube, pressed against the right wall as it travels towards the bottom of the tube. Finally, the ceramic bead (22) impacts the bottom of the tube in FIG. 3D.

Operation

Example 1

1. A sample to be ground or homogenized, if liquid is present, is inserted into a sample vial (20) that has preloaded hard grinding matrices [ceramic beads(22)] inside.
2. The vial (20) is sealed and inserted into the holder (18) of the device.
3. The device is turned on for a set period of time (usually 5 seconds or less, for example) at about 4,000 to 5,000 cycles per second to cause the sample to be ground or homogenized.
4. The tube is removed from the holder and unsealed to remove the ground sample for analysis.

Example 2

1. The user determines the optimal location for the holder on the connecting linkage.
2. The holder is attached onto the connecting linkage at the predetermined optimal location (distance from the crank pivot) to allow optimal grinding or homogenization of a sample.
3. A sample to be ground or homogenized, if liquid is present, is inserted into a sample vial (20) that has preloaded hard grinding matrices [ceramic beads (22)] inside.
4. The vial (20) is sealed and inserted into the holder (18) of the device.

5. The device is turned on for a set period of time (usually 5 seconds or less, for example) at about 4,000 to 5,000 cycles per second to cause the sample to be ground or homogenized.
6. The tube is removed from the holder and unsealed to remove the ground sample for analysis.

CONCLUDING STATEMENTS

All patents, provisional applications, patent applications and other publications mentioned in this specification are herein incorporated by reference.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those of skill in the art without departing from the scope and spirit of this invention. The scope of the invention is, therefore, indicated by the following claims rather than by the foregoing description. All changes, modifications, and variations coming within the meaning and range of equivalency of the claims are to be considered within their scope.

Furthermore, those skilled in the art will recognize, or be able to ascertain, using no more than routine experimentation, many equivalents to the specific embodiments of the invention described herein. Such equivalents are intended to be encompassed by the following claims.

What is claimed is:

1. An apparatus generating a reciprocating motion for the purpose of grinding or homogenizing samples, the apparatus comprising:
    a connecting linkage having a proximal end and a distal end, the connecting linkage extending along a longitudinal axis between the proximal end and the distal end;
    a holder, to hold a sample vial, attached to the connecting linkage between the proximal end and the distal end along the longitudinal axis of the connecting linkage, the holder forming a cavity having a cavity axial length that is configured to secure the sample vial;
    a crank operatively connected to the proximal end of the connecting linkage, the crank configured to impart rotational motion to the proximal end of the connecting linkage, wherein the crank has a diameter that is greater than or equal to the cavity axial length;
    a sliding carriage operatively connected to the distal end of the connecting linkage, the sliding carriage configured to restrict the distal end of the connecting linkage to a linear path; and
    a motor operatively connected to the crank to rotate the crank such that the holder, in use, moves with a combination of rotational and linear motion.

2. The apparatus of claim 1 wherein the cavity axial length is less than or equal to 1.5 inches.

3. The apparatus of claim 1 wherein the holder attachment onto the connecting linkage is adjustable such that the holder is configured to be relocated along the longitudinal axis of the connecting linkage.

4. The apparatus of claim 1 wherein the holder moves in an elliptical path in use, the elliptical path having a major axis that is greater than or equal to the cavity axial length.

5. The apparatus of claim 1 wherein the connecting linkage is less than or equal to 7.3 inches long.

6. The apparatus of claim 1 wherein, in use, the motor is configured to cause the holder to experience a reciprocation rate of between 4,000 and 5,000 cycles per minute.

7. An apparatus generating a reciprocating motion for the purpose of grinding or homogenizing samples, the apparatus comprising:
- a connecting linkage having a proximal end and a distal end;
- a crank configured to rotate about a central axis;
- a crank pivot coupled to the crank at a position away from the central axis of the crank and coupled to the connecting linkage at the proximal end of the connecting linkage such that as the crank rotates the proximal end of the connecting linkage undergoes rotational motion;
- a sliding carriage configured to slide along a rail;
- a slide pivot coupled to the sliding carriage and coupled to the connecting linkage at the distal end of the connecting linkage such that as the crank rotates the distal end of the connecting linkage undergoes linear motion;
- a holder configured to hold a sample vial, the holder attached to the connecting linkage between the proximal end and the distal end such that as the crank rotates the sample vial undergoes a combination of rotational and linear motion.

8. The apparatus of claim 7 wherein the holder forms a cavity to secure the sample vial as the holder undergoes the combination of rotational and linear motion.

9. The apparatus of claim 7 further comprising a second holder coupled to the connecting linkage.

10. The apparatus of claim 7 wherein the holder is configured to hold a plurality of sample vials.

11. The apparatus of claim 10 wherein the holder forms a plurality of cavities to secure the corresponding plurality of sample vials.

12. A mechanical reciprocating apparatus to grind or homogenize samples, the apparatus comprising:
- a holder configured to hold a sample vial;
- a connecting linkage having a proximal pivot point and a distal pivot point, the holder being attached to the connecting linkage between the proximal pivot point and the distal pivot point;
- a frame top;
- a rail coupled to the frame top;
- a crank pivot connected to the proximal pivot point of the connecting linkage;
- a slide pivot connected to the distal pivot point of the connecting linkage;
- a sliding carriage coupled to the slide pivot and to the rail such that the sliding carriage is configured to slide along the rail thereby causing the slide pivot to undergo linear motion; and
- a crank attached to the crank pivot and positioned between the connecting linkage and the frame top.

13. The apparatus of claim 12 wherein the connecting linkage is configured to accommodate multiple holders.

14. The apparatus of claim 12 further comprising a frame bottom coupled to the frame top using one or more spacers to maintain the frame bottom a fixed distance from the frame top.

15. The apparatus of claim 14 further comprising:
- a small pully positioned between the frame top and the frame bottom;
- a small pulley shaft operatively coupled to the small pully such that rotation of the small pulley shaft causes the small pully to rotate;
- a big pully positioned between the frame top and the frame bottom;
- a big pully shaft coupled to the big pully and to the crank such that rotation of the big pully causes the crank to rotate by way of the big pully shaft; and
- a drive belt coupled to the big pully and to the small pully wherein rotation of the small pully causes the big pully to rotate by way of the drive belt.

16. The apparatus of claim 15 further comprising a threaded adapter coupled to the frame bottom and configured to couple to a motor to provide an operative coupling between the small pulley and the motor so that rotation of the motor causes rotation of the small pulley by way of the small pully shaft.

17. The apparatus of claim 12 wherein the holder forms a cavity having a cavity axial length that is configured to secure a sample vial.

18. The apparatus of claim 17 wherein a diameter of rotational motion of the crank pivot is greater than or equal to the cavity axial length.

19. The apparatus of claim 17 wherein at least a portion of the holder is configured to move in an elliptical path that has a major axis that is greater than or equal to the cavity axial length.

20. The apparatus of claim 12 wherein the holder is configured to be attached at a plurality of locations on the connecting linkage to adjust the characteristics of motion of the holder.

* * * * *